United States Patent [19]

Young

[11] Patent Number: 4,542,138

[45] Date of Patent: Sep. 17, 1985

[54] DIOXOBENZOCYCLO-HEPTA-PYRIDINE COMPOUNDS, PROCESS AND USE AS ANTIHYPERTENSIVES

[75] Inventor: Steven D. Young, Lansdale, Pa.

[73] Assignee: Merck & Co., Inc., Rahway, N.J.

[21] Appl. No.: 608,292

[22] Filed: May 8, 1984

[51] Int. Cl.[4] .................. C07D 221/06; A61K 31/45
[52] U.S. Cl. ...................................... 514/290; 546/93
[58] Field of Search ......................... 546/93; 124/266

[56] References Cited

PUBLICATIONS

Mahn et al., *Appln. of the Mannich . . . Decane, Acta Chim.*, 1972, 17, 193–199 (Eng.) Chem Abs. 432233f.

Primary Examiner—Henry R. Jiles
Assistant Examiner—Patrica Ann Bucci
Attorney, Agent, or Firm—Joseph F. DiPrima; Alice O. Robertson; Michael C. Sudol

[57] ABSTRACT 6H-3,11b-Dihydrocarbalkoxy-5,7-dioxobenzo[6,7]cyclohepta[1,2-c]pyridine compounds represented by the formula:

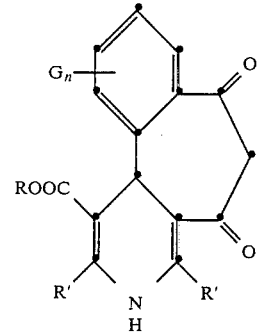

wherein G is lower alkyl or halogen; R is lower alkyl, R' is hydrogen, lower alkyl, and n is from 0 to 2 and a process for their preparation are disclosed. The compounds have the property of inhibiting calcium induced contraction of the smooth muscle.

5 Claims, No Drawings

DIOXOBENZOCYCLO-HEPTA-PYRIDINE COMPOUNDS, PROCESS AND USE AS ANTIHYPERTENSIVES

DESCRIPTION OF THE INVENTION

The present invention is directed to dioxobenzocycloheptapyridine compounds, more specifically to 6H-3,11b-dihydrocarbalkoxy-5,7-dioxobenzo[6,7]cyclohepta-[1,2-c]pyridine compounds represented by the formula

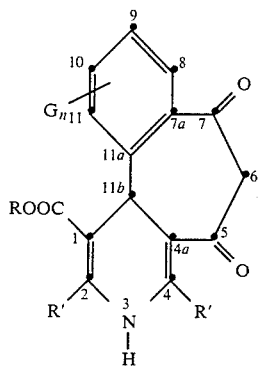

(I)

In this and suceeding formulas, G is lower alkyl or halogen, R is lower alkyl, R' is hydrogen or lower alkyl and n is from 0 to 2. By "lower alkyl" as herein employed are those alkyl groups having from 1 to 6 carbon atoms. Preferred lower alkyl groups are methyl and ethyl. By halogen is meant any halogen, i.e., chlorine, bromine, fluorine or iodine.

The products of the present invention are solids, soluble in most organic solvents. The products have several useful pharmacological properties rendering them adaptable for therapeutic applications. Thus, the compounds have shown properties which would render them useful as calcium entry blockers.

The compounds of the present invention may be prepared by intimately contacting a dihydropyridine compound of the formula

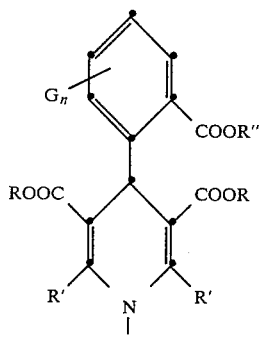

(II)

with trimethylaluminum in an inert environment.

In the dihydropyridine compound of Formula II, G, R and R' are as previously defined. R'' may be the same as R or may be different. Generally, it is methyl or ethyl for, since it is eliminated during the synthesis, it serves no purpose to employ a higher ester group in that position. However, if a higher ester group material is already available, it may be employed.

The condensing agent is trimethylaluminum. The agent appears to be unique for accomplishing the present synthesis. Triethylaluminum has been found to be unsatisfactory. Trimethylaluminum is available commercially as a solution in toluene and is employed in solution.

About equimolar amounts of the dihydropyridine compound and trimethylaluminum are employed. Preferably, a slight excess of the trimethylaluminum reagent is employed.

The reaction is carried out in an inert solvent medium. The inert solvent acts as a dispersing agent for the dihydropyridine reactant which is insoluble therein but then serves as a solvent when the reaction takes place with the formation of a soluble product. Suitable solvents include aromatic hydrocarbon solvents such as toluene, xylenes, benzene and the like. Since the dihydropyridine reactant is only slightly soluble, suitable provision is made for stirring or mixing.

The atmosphere for carrying out the reaction is also inert. This may be accomplished by providing an atmosphere of nitrogen or argon.

In carrying out the reaction, a solution of trimethylaluminum is added to a dispersion of the dihydropyridine compound of Formula II in an inert solvent at ambient temperature while the mixture is stirred and the resulting mixture then heated to reflux temperature and maintained at this temperature for time sufficient to complete the reaction with the formation of the desired dioxobenzocycloheptapyridine compound of Formula I. Although the reaction appears to take place quickly, the mixture is heated for several hours to assure completion of the formation of the product. The product may be recovered from the reaction mixture by diluting the reaction mixture with a suitable water-immiscible solvent, washing the resulting solution successively with dilute acid, sodium bicarbonate solution and brine, thereafter drying the solution, and then evaporating the solvent from the dried solution to obtain the product as residue. Ethyl acetate has been found to be a useful solvent in the recovery steps. Other suitable solvents include ethyl ether, chloroform, methylene chloride and the like. Usually a solid drying agent such as magnesium sulfate is employed for drying so that it must be removed by filtration before recovering the product. The product may be purified by conventional procedures, preferably chromatography on silica gel employing ethyl acetate-hexane as eluant in a method referred to as Still or flash chromatography described in J. Org. Chem. 43, 2923 (1978).

The compounds of the present invention possess pharmacological properties adaptable for therapeutic uses. One of the properties demonstrated is the inhibition of calcium induced contraction of tracheal smooth muscle or vascular tissue. The property may be observed in a test in which segments of tracheal smooth muscle obtained from male Sprague-Dawley rats are suspended in physiological salt solution in a tissue bath instrumented for recording contractions. After the tissue has been equilibrated, washed in calcium-free physiological salt solution and then depolarized, 1.0 mM calcium chloride is re-added to induce contraction. After the contraction has reached a plateau, tissues are washed and a test compound or vehicle is added to determine the effect on a second contraction achieved by the above cyclic protocol. From measuring the initial contraction as well as the second contraction in the presence of the test compound, the extent of inhibition may be calculated.

In this test, 6H-3,11b-dihydro-1-carbomethoxy-2,4-dimethyl-5,7-dioxobenzo[6,7]cyclohepta [1,2-c]pyridine showed 36 percent inhibition at $10^{-6}$ M. This indicates usefulness of the compounds in the study and treatment of cardiovascular diseases.

For use in the chemotherapeutic treatment of various diseases, an effective amount of the compounds of the present invention may be administered orally, parenterally, by inhalation, or by suppository, and in any suitable dosage form. For oral administration, the compounds may be offered in the form of tablets or capsules with suitable dispersants and carrier materials or dispersed in a liquid carrier for administration as solution or aqueous dispersion or emulsion; for parenteral administration, the compounds may be dispersed in an appropriate liquid carrier with or without dispersing agents depending on whether a solution, emulsion or other dispersion is intended; for aerosol administration the compound may be dispersed formulated with a suitable dispersant and propellant; and for use as suppository the compounds may be dispersed in a suitable carrier. Suitable carriers and dispersants are hereinafter described.

The ratio of the compound of the present invention to carrier varies with the particular compound, purpose and the mode of administration. The dosage level for the compounds may be varied from about 0.5 milligram to about 7.0 milligrams per kilogram of body weight per day. Daily doses in the range of 1 to 3.5 mg/kg are preferred. These doses are suitable for any of the utilities described herein.

The compounds may be formulated with a pharmaceutical carrier or diluent.

To prepare the pharmaceutical compositions of this invention, the compound of Formula (I) as the active ingredient is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for such example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, although other ingredients may be included, for purposes such as, for example, for aiding solubility or for preservation. Injectable suspensions also may be prepared, in which case appropriate liquid carriers, suspending agents and the like may be employed. The pharmaceutical compositions herein will contain, per dosage unit, e.g., tablet, capsule, powder, injection, teaspoonful and the like, from about 10 to about 500 mg. of the active ingredient, preferably, from about 10 to about 250 mg.

The following examples illustrate the invention but are not to be construed as limiting:

EXAMPLE 1

6H-3,11b-Dihydro-1-carbomethoxy-2,4-dimethyl-5,7-dioxobenzo[6,7]-cyclohepta[1,2-c]pyridine

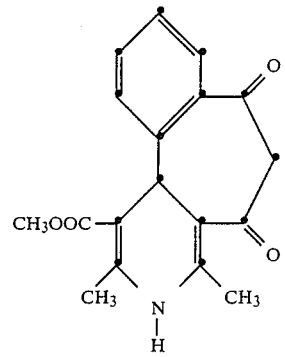

0.61 milliliter of 2M trimethylaluminum (88.3 milligrams, 1.22 millimoles) was added with stirring under an atmosphere of argon to 400 milligrams (1.11 millimoles) of dimethyl 2,6-dimethyl-4-(2-carbomethoxyphenyl)-1,4-dihydropyridine-3,5-dicarboxylate and 20 milliliters of dry toluene whereupon the reaction mixture turned yellow and all of the dihydropyridine compound dissolved. The resulting mixture was heated to reflux temperature and maintained at this temperature for 3.5 hours. The mixture was allowed to cool to room temperature, then diluted with ethyl acetate and the ethyl acetate solution washed successively with 2N hydrochloric acid, sodium bicarbonate solution and brine. The washed solution was dried over magnesium sulfate, the drying agent filtered off and the filtrate subjected to reduced pressure to vaporize the solvent and recover a yellow oil as residue. The residue was subjected to flash chromatography on silica gel employing 50 percent ethyl acetate-50 percent hexane as eluant to obtain 142 milligrams of a 6H-3,11b-dihydro-1-carbomethoxy-2,4-dimethyl-5,7-dioxobenzo[6,7]-cyclohepta[1,2-c]pyridine product as a purified yellow oil which crystallized from ethyl ether as 130 milligrams of orange crystals, m.p. 233°–235° C. The product had elemental analyses as follows:

Calcd. for $C_{18}H_{17}NO_4$ (m.w. 311.3)—C, 69.44; H, 5.50; N, 4.50. Found: C, 69.35; H, 5.64; N, 4.57.

EXAMPLE 2

6H-3,11b-Dihydro-1-carboisopropoxy-10-chloro-2,4-diethyl-5,7-dioxobenzo[6,7]cyclohepta[1,2-c]pyridine

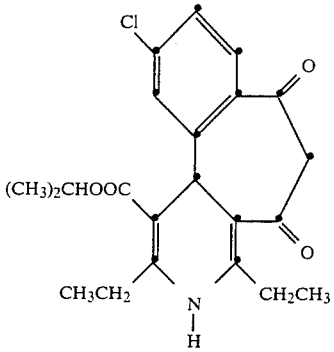

In a reaction carried out in a manner similar to that described in Example 1, 0.61 milliliter of 2M trimethylaluminum (1.22 millimoles) is added with stirring under an atmosphere of argon to 499 milligrams (1.11 millimoles) of diisopropyl 4-(2-carbomethoxy-5-chlorophenyl)-2,6-diethyl-1,4-dihydropyridine-3,5-dicarboxylate in 20 milliliters of dry toluene. After completion of the addition, the mixture is heated at reflux temperature for two hours, allowed to cool, then diluted with ethyl acetate. The ethyl acetate solution is washed with 2N hydrochloric acid, sodium bicarbonate solution and brine, dried, the drying agent filtered off and the filtrate subjected to reduced pressure to vaporize the solvent and to recover as residue the desired 6H-3,11b-dihydro-1-carboisopropoxy-2,4-diethyl-5,7-dioxobenzo-[6,7]cyclohepta[1,2-c]pyridine product.

EXAMPLE 3

6H-3,11b-Dihydro-1-carbomethoxy-9-isopropyl-2,4-dimethyl-5,7-dioxobenzo[6,7]cyclohepta[1,2-c]pyridine

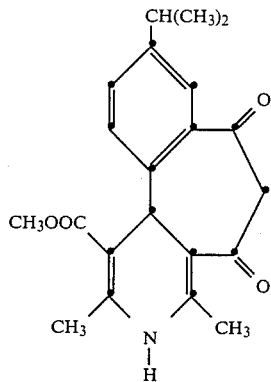

In a similar manner, 0.61 milliliter of 2M trimethylaluminum (1.22 millimoles) is added, while stirring at ambient temperature under an atmosphere of argon, to 446 milligrams (1.11 millimoles) of dimethyl 2,6-dimethyl-4-(2-carbomethoxy-4-isopropylphenyl)-1,4-dihydropyridine-3,5-dicarboxylate in 20 milliliters of dry toluene, and the mixture heated at reflux temperature for several hours. The mixture is then allowed to cool, diluted with ethyl acetate, the diluted solution washed as previously described, dried, and the solvent evaporated to obtain 6H-3,11b-dihydro-1-carbethoxy-9-isopropyl-2,4-dimethyl-5,7-dioxobenzo[6,7]cyclohepta[1,2-c]pyridine product as residue. The product is purified by flash chromatography on silica gel employing 1:1 ethyl acetate/hexane as eluant.

EXAMPLE 4

6H-3,11b-Dihydro-1-carbomethoxy-9,10-dimethyl-5,7-dioxobenzo[6,7]cyclohepta[1,2-c]pyridine

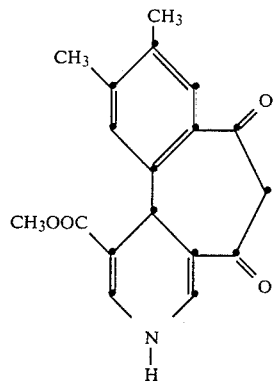

In a similar manner, 0.61 milliliter of 2M trimethylaluminum (1.22 millimoles) is added with stirring under argon atmosphere to 400 milligrams (1.11 millimoles) of dimethyl 4-(2-carbomethoxy-4,5-dimethylphenyl)-1,4-dihydropyridine-3,5-dicarboxylate in 20 milliliters of dry toluene, and the resulting mixture heated at reflux temperature for several hours. The mixture is then allowed to cool, diluted with ethyl acetate, the diluted solution washed as previously described, dried, and the solvent evaporated to obtain 6H-3,11b-dihydro-1-carbomethoxy-9,10-dimethyl-5,7-dioxobenzo[6,7]cyclohepta[1,2-c]pyridine product as residue.

EXAMPLE 5

In operations carried out in a manner similar to that described in the foregoing examples, the following compounds may be prepared from the indicated dihydropyridine compound and trimethylaluminum:

6H-3,11b-Dihydro-1-(carbo-n-hexyloxy)-9-isopropyl-2,4-dimethyl-5,7-dioxobenzo[6,7]cyclohepta[1,2-c]pyridine from di-n-hexyl 2,6-dimethyl-4-(2-carbomethoxy-4-isopropylphenyl)-1,4-dihydropyridine-3,5-dicarboxylate.

6H-3,11b-Dihydro-1-carbethoxy-9-t-butyl-2,4-dimethyl-5,7-dioxobenzo-[6,7]cyclohepta[1,2-c]pyridine from diethyl 2,6-dimethyl-4-(2-carboethoxy-4-t-butylphenyl)-1,4-dihydropyridine-3,5-dicarboxylate.

6H-3,11b-Dihydro-1-carbomethoxy-10-fluoro-2,4-diethyl-5,7-dioxobenzo[6,7]cyclohepta[1,2-c]pyridine from dimethyl 2,6-diethyl-4-(2-carbethoxy-3-fluorophenyl)-1,4-dihydropyridine-3,5-dicarboxylate.

6H-3,11b-Dihydro-1-carbethoxy-9-bromo-2,4-dimethyl-5,7-dioxobenzo[6,7]cyclohepta[1,2-c]pyridine from diethyl 2,6-dimethyl-4-(4-bromo-2-carbethoxyphenyl)-1,4-dihydropyridine-3,5-dicarboxylate.

6H-3,11b-Dihydro-1-carbomethoxy-9,10-dichloro-2,4-dimethyl-5,7-dioxobenzo[6,7]cyclohepta [1,2-c]pyridine from dimethyl 2,6-dimethyl-4-(2-carbomethoxy-3,4-dichlorophenyl)-1,4-dihydropyridine-3,5-dicarboxylate.

6H-3,11b-Dihydro-1-carbomethoxy-2,4,9,10-tetramethyl-5,7-dioxobenzo[6,7]cyclohepta[1,2-c]pyridine from dimethyl 2,6-dimethyl-4-(2-carbomethoxy-4,5-dimethylphenyl)-1,4-dihydropyridine-3,5-dicarboxylate.

6H-3,11b-Dihydro-1-(carbo-n-pentyloxy)-10-iodo-2,4-dimethyl-5,7-dioxobenzo[6,7]cyclohepta[1,2-c]pyridine from di-n-pentyl 2,6-dimethyl-4-(2-carbomethoxy-5-chlorophenyl)-1,4-dihydropyridine-3,5-dicarboxylate.

PREPARATION OF STARTING MATERIAL

The o-carbalkoxyphenyldihydropyridine compound starting material of Formula II may be prepared by heating together substantially equimolar proportions of an o-carbalkoxy substituted-aromatic aldehyde, 2-acylacetic acid ester and a 3-amino-2,3-alkenoic acid ester in a polar solvent such as ethanol for time sufficient to complete the reaction with the formation of the compound of Formula II and water by-product which is codistilled with ethanol. The product then may be recovered and purified employing conventional procedures.

When the desired product is one in which there are no substituents in the 2 and 4 positions, the starting compound (Formula II) is prepared from o-carbalkoxy-substituted-aromatic aldehyde, formyl acetic ester and 3-aminoacrylic ester. When both R's are to be the same, it is necessary to select 2-acylacetic and 3-amino-2,3-alkenoic acids of the same chain length. In the preferred embodiment of the present invention, the alkyl groups in the 2 and 4 positions are methyl so that the esters condensed with the appropriate aromatic aldehyde are acetoacetic ester and β-aminocrotonic ester.

What is claimed is:

1. A dioxobenzocycloheptapyridine compound represented by the formula

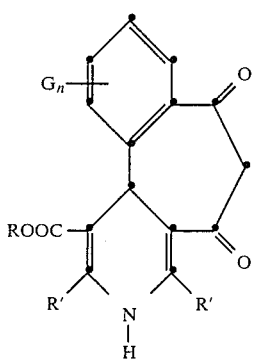

wherein G is lower alkyl or halogen; R is lower alkyl, R' is hydrogen, lower alkyl, and n is from 0 to 2.

2. A compound according to claim 1 in which R is methyl, R' is methyl and n is 0, which compound is named 6H-3,11b-dihydro-1-carbomethoxy-2,4-dimethyl-5,7-dioxobenzo[6,7]cyclohepta[1,2-c]pyridine.

3. A process for preparing a dioxobenzocycloheptapyridine compound represented by the formula

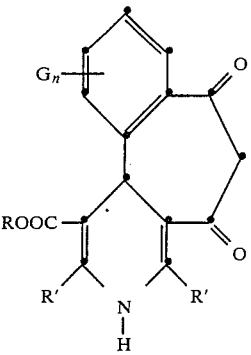

wherein G is lower alkyl or halogen, R is lower alkyl, R' is hydrogen or lower alkyl and n is from 0 to 2, which comprises intimately contacting an dihydropyridine compound of the formula

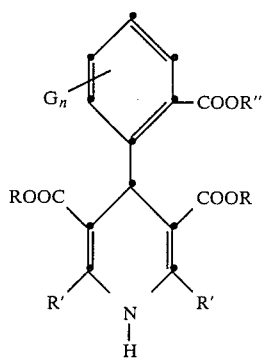

wherein G, R and R' are as previously defined and R" is a lower alkyl group with a solution of trimethylaluminum in an inert solvent as reaction medium and in an inert atmosphere.

4. A composition useful in the treatment of hypertension comprising a non-toxic therapeutically active amount of a compound having the formula:

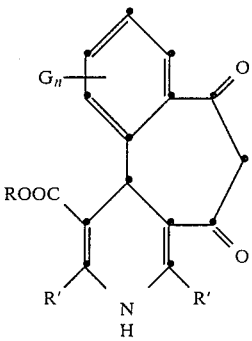

wherein G is lower alkyl or halogen, R is lower alkyl, R' is hydrogen or lower alkyl and n is from 0 to 2, in initmate admixture with a pharmaceutically acceptable carrier.

5. A method for treating hypertension which comprises administering a non-toxic therapeutically active amount of a compound having the structure:

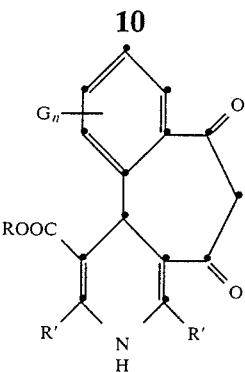
wherein G is loweralkyl or halogen, R is lower alkyl, R' is hydrogen or lower alkyl and n is from 0 to 2, in an intimate admixture with a pharmaceutically acceptable carrier.
* * * * *